US00PP15937P3

(12) United States Plant Patent
Meilland

(10) Patent No.: US PP15,937 P3
(45) Date of Patent: Sep. 6, 2005

(54) **HYBRID *RUGOSA* ROSE PLANT NAMED 'MEITOZAURE'**

(50) Latin Name: *Rosa rugosa*
Varietal Denomination: Meitozaure

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 162 days.

(21) Appl. No.: 10/737,918

(22) Filed: Dec. 18, 2003

(65) Prior Publication Data

US 2005/0138698 P1 Jun. 23, 2005

(51) Int. Cl.[7] ..... A01H 5/00
(52) U.S. Cl. ..... Plt./101

(58) Field of Search ..... Plt./107, 101, 102, Plt./108

*Primary Examiner*—Anne Marie Grunberg
*Assistant Examiner*—June Hwu
(74) *Attorney, Agent, or Firm*—Burns, Doane, Swecker & Mathis, LLP

(57) ABSTRACT

A new and distinct variety of *Rugosa* rose plant is provided which forms in clusters attractive single bright purplish-red blossoms having a strong fragrance. The blossom coloration is well maintained upon maturity. The plant exhibits a compact and typically broader than high growth habit with good vigor. Excellent resistance to Black Spot, Powdery Mildew and Downey Mildew is displayed. The very dense medium green to dark green foliage with a semi-glossy aspect contrasts nicely with the blossom coloration. The new variety is particularly well suited for growing as attractive ornamentation in the landscape and serves particularly well in small spaces and in mass plantings with minimal maintenance requirements.

3 Drawing Sheets

Botanical/commercial classification: *Rosa rugosa*/Hybrid *Rugosa* Rose Plant.
Varietal denomination: cv. 'Meitozaure'.

SUMMARY OF THE INVENTION

The new variety of Hybrid *Rugosa* rose plant was created by artificial pollination wherein two parents were crossed which previously had been studied in the hope that they would contribute the desired characteristics. The female parent (i.e., the seed parent) was the 'Flower Carpet White' variety (U.S. Plant Pat. No. 9,573). The 'Flower Carpet White' variety sometimes is known as the 'Noaschnee' variety. The male parent (i.e., the pollen parent) was 'Frau Dagmar Hartopp' variety (non-patented in the United States). The 'Frau Dagmar Hartopp' variety sometimes is known as the 'Frau Dagmar Hastrup' variety. The parentage of the new variety can be summarized as follows:

'Flower Carpet White'×'Frau Dagmar Hartopp'.

The seeds resulting from the above pollination were sown and small plants were obtained which were physically and biologically different from each other. Selective study resulted in the identification of a single plant of the new variety.

It was found that the new *Rugosa* rose variety of the present invention (a) exhibits a compact and typically broader than high growth habit with good vigor, (b) forms in clusters attractive single bright purplish-red blossoms that well retain their coloration upon maturity, (c) forms very dense medium green to dark green foliage having a semi-glossy aspect that contrasts well with the blossom coloration, (d) is highly resistant to common rose diseases such as Black Spot, Powdery Mildew and Downy Mildew, and (e) is particularly well suited for growing as attractive ornamentation in the landscape.

The new variety well meets the needs of the horticultural industry and can be grown to advantage in parks and gardens where attractive ornamentation is desired. It is particularly well suited for growing in small spaces and in mass plantings with minimal maintenance requirements.

The new variety can be readily distinguished from its ancestors. For instance, the 'Flower Carpet White' variety forms white blossoms and the 'Frau Dagmar Hartopp' variety forms dissimilar silvery-pink blossoms with a ripe fruit fragrance. Also, the 'Frau Dagmar Hartopp' variety forms red hips in abundance while the new variety commonly forms orange hips in a lesser quantity.

Additionally, the new variety can be readily distinguished from the Hybrid *Rugosa* 'Strolon' variety (non-patented in the United States) which exhibits medium pink blossoms. Such comparative variety sometimes is known as the 'Polarsonne' variety.

The new variety has been found to undergo asexual propagation at West Grove, Pa., U.S.A., and at Wasco, Calif., U.S.A., by a number of routes, including budding, grafting, and by the use of cuttings. Asexual propagation by the above-mentioned techniques at Pennsylvania, and California, has shown that the characteristics of the new variety are stable and are strictly transmissible by such asexual propagation from one generation to another. Good plant development is displayed regardless of the mode of asexual propagation.

The new variety has been named the 'Meitozaure' variety.

BRIEF DESCRIPTION OF THE PHOTOGRAPHS

The accompanying photographs show as nearly true as it is reasonably possible to make the same, in a color illustrations of this character, typical specimens of the new variety. The rose plants of the new variety were approximately four years of age and were photographed during June 2003 while growing outdoors on their own roots in the ground at Jennersville, Pa. U.S.A.

DETAILED DESCRIPTION

Figure 1:
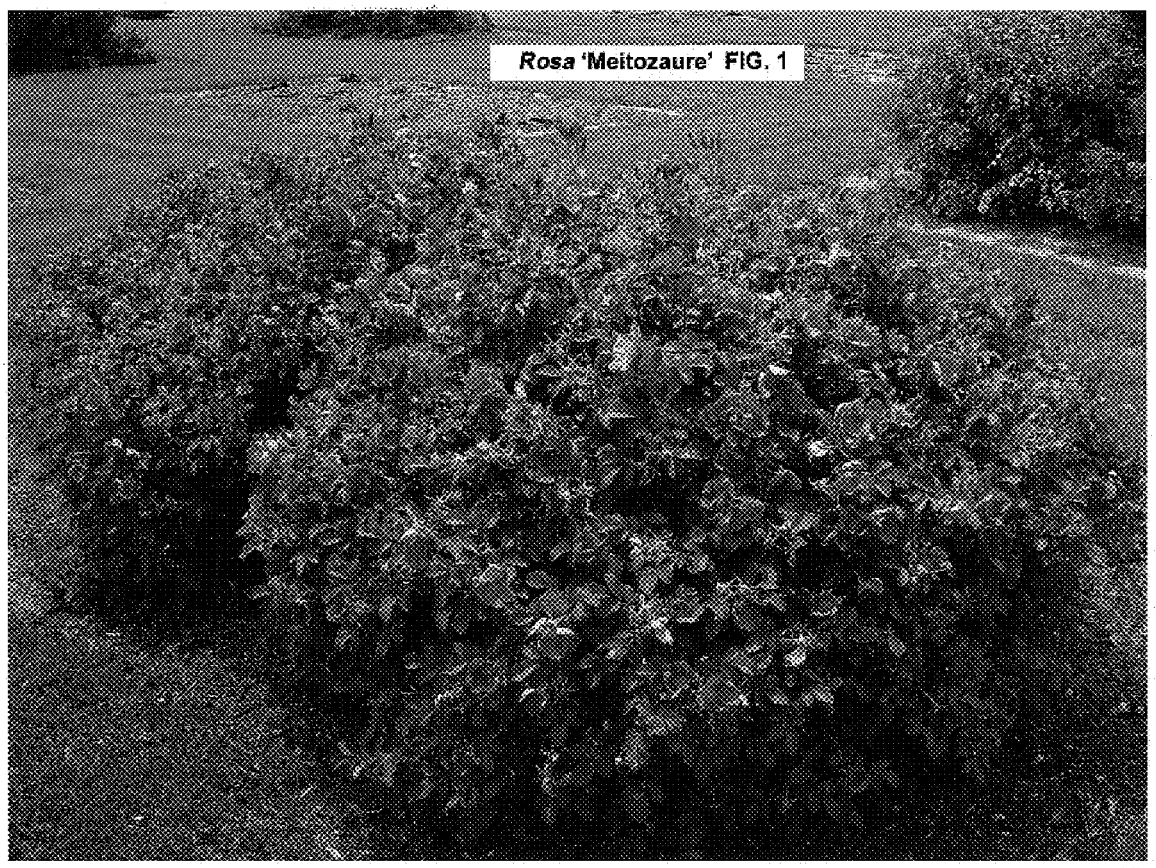
FIG. 1 illustrates an overall view of a typical plant that had been cut to a height of approximately 10 inches during the previous winter.
Figure 2:
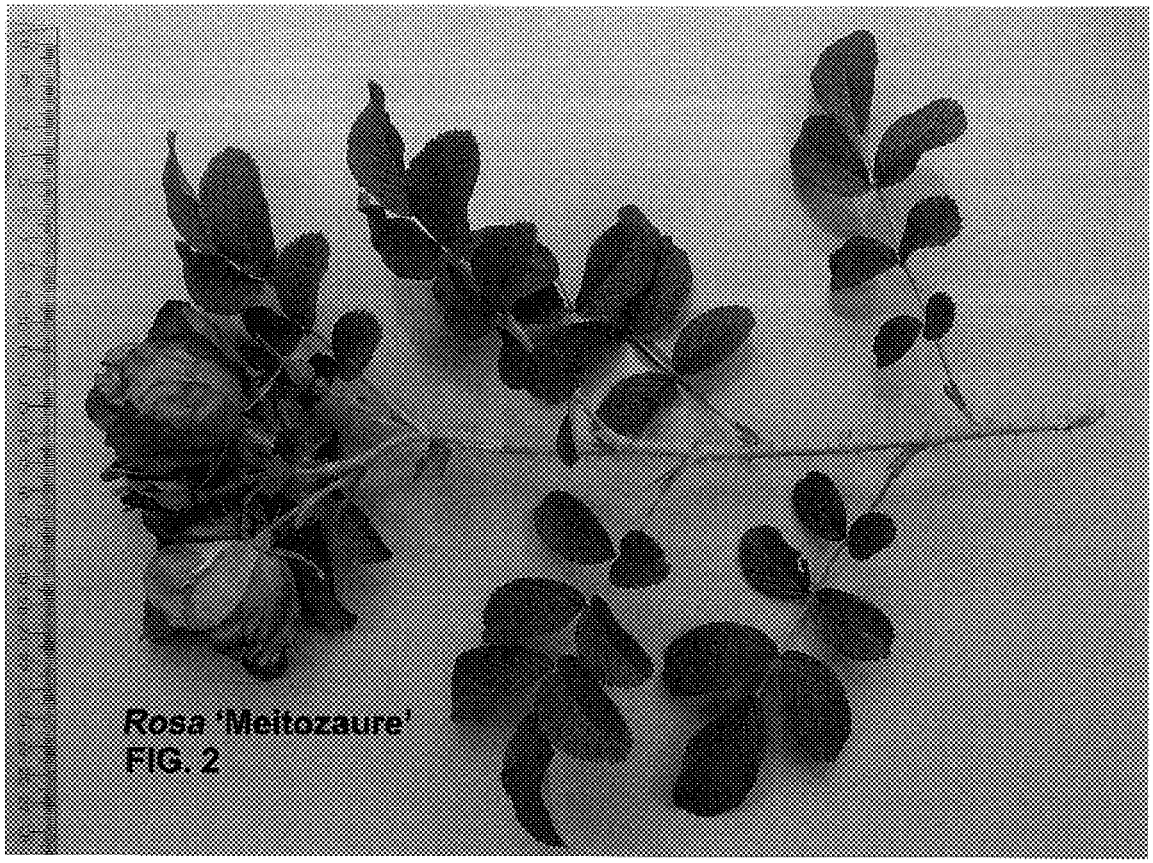
FIG. 2 illustrates a specimen of a typical flowering stem with foliage.
Figure 3:
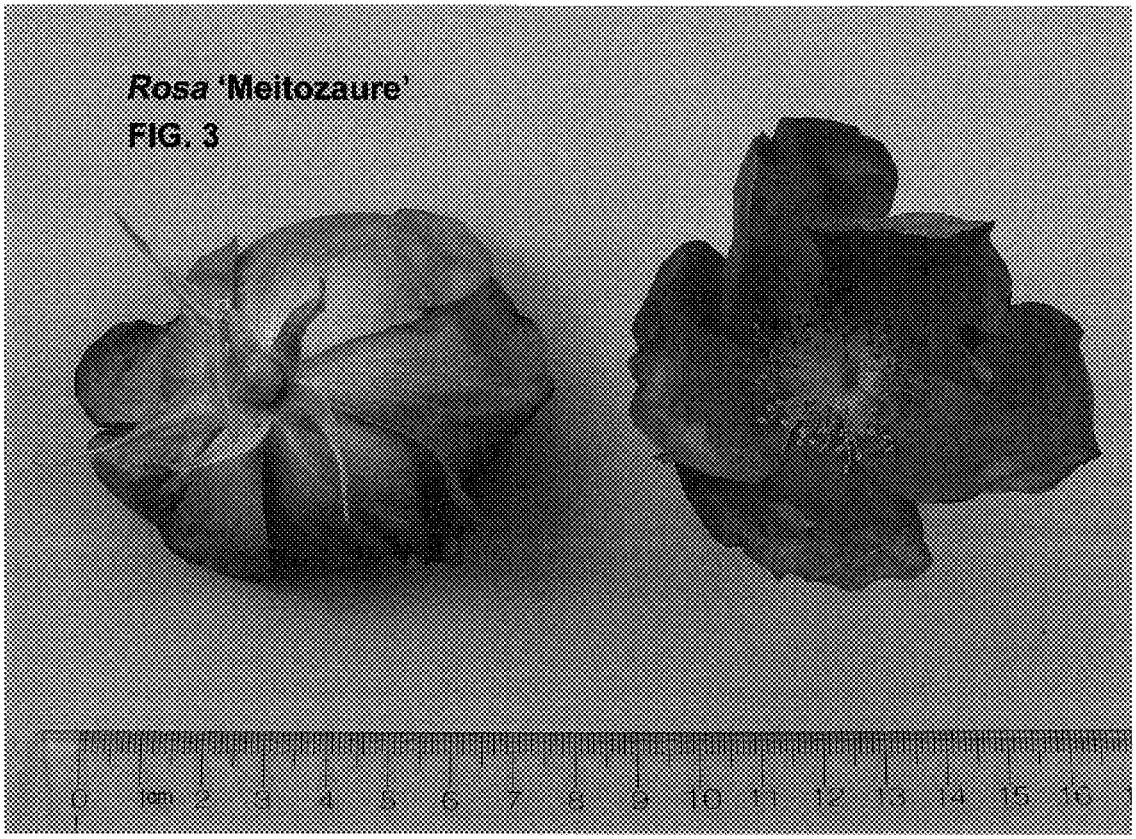
FIG. 3 illustrates specimens of typical flowers—plan view obverse on the right, and—plan view reverse on the left.

The chart used in the identification of the colors is that of The Royal Horticultural Society (R.H.S. Colour Chart). The description is based on the observation of four year-old plants during June, 2003 while growing outdoors on their own roots at Jennersville, Pa.

Class: Hybrid *Rugosa*.

Plant:

*Height.*—Approximately 0.5 to 0.75 m on average at the end of the growing season.

*Width.*—Approximately 1.5 to 2.5 m on average at the end of the growing season.

*Habit.*—Compact, spreading, and bushy.

Branches:

*Wood.*—New wood is near Yellow-Green Group 145B in coloration and is covered with relatively soft prickles, and old wood is near Greyed-Green Group 197A in coloration and is covered with stiff prickles.

*Thorns.*—Size: Variable and commonly approximately 2 to 6 mm in length. Quantity: Numerous. Shape: Triangularis. Color: Near Yellow-Green Group 145B when immature and near Yellow-Green Group 150C when mature.

Leaves:

*Size.*—Varies widely within and between leaflet numbers. Mature 7-leaflet leaves typically are approximately 12 to 16 cm (approximately 14 cm on average) in length, and approximately 7 to 9 cm (approximately 8.4 cm on average) in width. Mature 9-leaflet leaves typically are approximately 14 to 16 cm (approximately 15 cm on average) in length, and approximately 7 to 10 cm (approximately 8.6 cm on average) in width.

*Petioles.*—Approximately 32 mm in length on average, glabrous on the upper surface, prickly on the under surface, and near Yellow-Green Group 145C in coloration. The rachis is similarly glabrous on the upper surface and prickly on the under surface.

*Stipules.*—Adnate, relatively smooth, pectinate, and commonly measure approximately 10×17 mm on average. The upper surface is near Yellow-Green Group 145A at the base and darkens to Green Group 137D at the apex. The lower surface is near Yellow-Green Group 145B. The midrib on both surfaces is near Green Group 138B.

*Leaflets.*—Number: Rarely 3 and if present commonly associated with an inflorescence, rarely 5, 7 (most often), and occasionally 9. Arrangement: Alternate and pinnately compound. Venation: Pinnate and reticulate. Shape: Typically elliptical to oblong to slightly obovate. Apex: Varies from commonly truncate to nearly truncate to rounded to broadly obtuse to obtuse to broadly acute to broadly acuminate. Base: Typically oblique to rounded to occasionally broadly cuneate. Margin: Typically serrate with the teeth being more prominent toward the apex to rarely crenate. Texture: Rugose and coriaceus. Size terminal leaflets: From a mature 7-leaflet leaf typically from approximately 38 to 50 mm (approximately 43.5 mm on average) in length, and approximately 25 to 31 mm (approximately 29 mm on average) in width. From a mature 9-leaflet leaf typically from approximately 43 to 45 mm (approximately 44 mm on average) in length and approximately 26 to 30 mm (approximately 28 mm) in width. Color (adult foliage): Upper surface: Darker leaves are near Green Group 136A and Green Group 139A, and lighter leaves are near Green Group 137A. Under surface: Darker leaves are near Green Group 137C and lighter leaves are near Greyed-Green Group 191A.

Inflorescence:

*Number of flowers.*—Commonly 1 to 7 per stem, and approximately 5 on average. However, as many as 14 blossoms have been observed on a very vigorous stem.

*Bearing.*—Borne terminally on the axils of the uppermost part of the stem. Heaviest with the first flush in June, and continuous but less floriferous until hard frost.

*Type.*—Complete, perfect, polypetalous, and actinomorphic.

*Sepals.*—Number: Typically 5, and very rarely 4 or 6. Extensions: When present feathery foliaceous extensions at the tip commonly may range from approximately 5 to 8.5 mm in length. Shape: Typically lanceolate with some minor feathering at the tip. Texture: Smooth on the inner surface and glandular on the outer surface.

*Peduncles.*—Length: Commonly approximately 23 mm on average. Surface texture: Pubescent. Strength: Quite strong. Color: Yellow-Green Group 144B and 144C. Size: Typically approximately 20 to 46 mm (approximately 35 mm in length on average), and approximately 5 to 8 mm (approximately 6 mm) in width on average. Color: Near Yellow-Green Group 144D on the inner surface and near 144B and 144C on the outer surface.

*Flower.*—Shape: Single and flattened cup-shaped when fully open. Diameter: Approximately 6 to 8 cm on average. Color (fully open blossom): Upper surface: Typically near Red-Purple Group 71B, 71C, 72B, 72C, and 74A with some areas approaching Purple Group 77B and 78A and Purple-Violet Group 80B and 80C. Lower surface: Typically near Red-Purple Group 71D, 72B, and 72C and Purple Group 77C and 77D approaching the base of the petal. Base petal spot: On both surfaces a small area of White Group 155A shading towards and through White Group 155A and Green-White Group 157B becoming near Yellow Group 4D at the very base of the petal. Color stability: Very good with the coloration commonly being well maintained to fully maturity. Fragrance: Strong, spicy, sweet clove. Petal number: Commonly 5 per blossom under normal growing conditions. Petal shape: Broadly obovate to almost obcordate. Petaloids: None observed. Petal texture: Glabrous, smooth, somewhat membranaceus, and lightly crinkled. Petal margin: Typically entire and somewhat revolute at times. Petal apex: Truncate to emarginate to praemorsus to occasionally somewhat retuse. Petal base: Rounded to broadly rounded to broadly cuneate. Petal size: Typically approximately 3.5 to 4.6 cm in length and width. Petal drop: Good with the petals commonly detaching cleanly before drying. Stamen number: Typically approximately 175 to 250, and commonly approximately 190 to 200 on average. Anthers: Commonly approximately 1.1 to 1.8 mm in size with an average of approximately 1.4 mm, Greyed-Yellow Group 160A on the body, and some Greyed-Yellow Group 160B at the edges. Pollen: Abundant and near Greyed-Yellow Group 160A in coloration. Pistil number: Typically approximately 194 on average. Styles: Approximately 5.5 mm in length on average, and near Yellow-Green Group 150D in coloration. Stigmas: Near Yellow-Green Group 154B in coloration. Receptacle: Substantially round in shape, when the flower is fully open the length commonly is approximately 6 to 7 mm and the diameter commonly is approximately 7 to 9 mm. Hips: Showy and formed sporadically, sub-globose in shape, approximately 11 to 17 mm (near 14 mm on average) in length, approximately 13 to 23 mm (near 18 mm on average) in diameter, glabrous with a light glaucous covering, commonly soften with maturity, and the coloration commonly is near Red Group 46A in darker areas blended with some Orange-Red Group 31A and 34B and Greyed-Orange Group 169A, 169B, and 170A. Lastingness: A typical blossom commonly lasts approximately 5 days on the plant and approximately 3 days when cut and placed in a vase. Such longevity is influenced by the environmental conditions that are encountered.

Development:

*Vegetation.*—Strong and vigorous with typical shoots sometimes growing 0.75 to 1.2 m in a single growing season.

*Blooming.*—Very abundant, commonly heaviest with the first flush in June, and continuous but less floriferous until hard frost.

*Resistance to diseases.*—Excellent with respect to rose Black Spot (*Marssonina rosae*), Powdery Mildew (*Sphaerotheca*), and Downey Mildew (*Peronospora*).

Plants of the new 'Meitozaure' variety have not been observed under all possible environmental conditions to date. Accordingly, it is possible that the phenotypic expression may vary somewhat with changes in light intensity and duration, cultural practices, and other environmental conditions.

I claim:

1. A new and distinct variety of *Rugosa* rose plant characterized by the following combination of characteristics:

(a) exhibits a compact and typically broader than high growth habit with good vigor, (b) forms in clusters attractive single bright purplish-red blossoms that well retain their coloration upon maturity, (c) forms very dense medium green to dark green foliage having a semi-glossy aspect that contrasts well with the blossom coloration, (d) is highly resistant to common rose diseases such as Black Spot, Powdery Mildew and Downey Mildew, and (d) is particularly well suited for growing as attractive ornamentation in the landscape;

substantially as herein shown and described.

* * * * *

*Rosa* 'Meitozaure' FIG. 1

*Rosa* 'Meitozaure'

*Rosa* 'Meitozaure'